United States Patent [19]

Farnham

[11] Patent Number: 4,577,003
[45] Date of Patent: Mar. 18, 1986

[54] PENTACOORDINATE SILYL ENOLATES AND THEIR USE AS POLYMERIZATION INITIATORS

[75] Inventor: William B. Farnham, Wilmington, Del.

[73] Assignee: E. I. Du Pont de Nemours and Company, Wilmington, Del.

[21] Appl. No.: 716,481

[22] Filed: Mar. 27, 1985

Related U.S. Application Data

[62] Division of Ser. No. 619,944, Jun. 12, 1984, Pat. No. 4,528,389.

[51] Int. Cl.$^4$ ................................................ C08F 2/00
[52] U.S. Cl. .................................. 526/194; 526/329.7
[58] Field of Search .......................................... 526/194

[56] References Cited

U.S. PATENT DOCUMENTS 4,414,372 11/1983 Farnham et al. .
4,417,034 11/1983 Webster .
4,430,504 2/1984 Reuter et al. ........................ 526/194
4,447,628 5/1984 Farnham .

OTHER PUBLICATIONS

Noyori et al., J. Am. Chem. Soc. 99, 1265, (1977).
Noyori et al., J. Am. Chem. Soc. 102, 1223, (1980).
Farnham et al., J. Am. Chem. Soc. 103, 4608, (1981).
Perrozzi et al., J. Am. Chem. Soc. 101, 1591, (1979).

Primary Examiner—Joseph L. Schofer
Assistant Examiner—Peter F. Kulkosky

[57] ABSTRACT

Pentacoordinate silyl encolate and the use thereof as an initiator without a co-catalyst, in the polymerization of methacrylic monomers, such as methacrylate esters.

6 Claims, No Drawings

PENTACOORDINATE SILYL ENOLATES AND THEIR USE AS POLYMERIZATION INITIATORS

CROSS-REFERENCE TO RELATED APPLICATION

This is a division of application Ser. No. 619,944 filed June 12, 1984 and allowed Jan. 23, 1985, now U.S. Pat. No. 4,528,389.

BACKGROUND OF THE INVENTION

1. Field of Invention

This invention relates to pentacoordinate silyl enolates and to their use as polymerization initiators for methacrylic monomers, including methacrylate esters.

2. Background

Noyori et al., J. Am. Chem. Soc. 99, 1265 (1977); ibid 102, 1223 (1980) have proposed, without experimental support, pentacoordinate silicon-containing species as reactive intermediates in the fluoride-catalyzed addition of silyl enol ethers to carbonyl compounds such as aldehydes. There is no disclosure of the spirosilicate structures of the invention which is the basis of this application, which invention will be described in detail hereinafter.

U.S. Pat. No. 4,447,628 discloses anionic pentacoordinate silicates of the formula

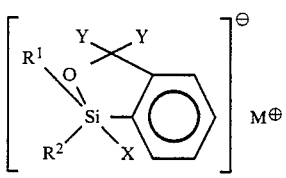

wherein:
R$^1$ and R$^2$ are both aryl or one is aryl and the other is C$_{1-4}$ alkyl, or R$^1$ and R$^2$ taken together are

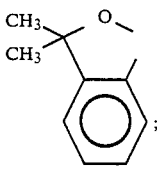

Y is CF$_3$ or, when R$^1$ and R$^2$ are taken together, CH$_3$;
X is F, CN or N$_3$ when Y is CF$_3$;
X is F when Y is CH$_3$;
M$^\oplus$ is (R$^3$)$_4$N$^\oplus$, [(R$^4$)$_2$N]$_3$S$^\oplus$ or Cs$^\oplus$ when X is F;
M$^\oplus$ is (R$^5$)$_4$N$^\oplus$ when X is CN;
M$^\oplus$ is [(R$^4$)$_2$N]$_3$S$^\oplus$ or (R$^5$)$_4$N$^\oplus$ when X is N$_3$;
aryl is phenyl, phenyl substituted with F, C$_{1-4}$ alkyl or C$_{1-4}$ alkoxy, or naphthyl;
R$^3$ is C$_{1-4}$ alkyl;
R$^4$ is C$_{1-2}$ alkyl or (R$^4$)$_2$ is (CH$_2$)$_5$; and
R$^5$ is C$_{2-4}$ alkyl.

The silicates are useful as catalysts for the polymerization of methyl methacrylate in the presence of selected silicon-containing initiators such as [(1-methoxy-2-methyl-1-propenyl)oxy]trimethylsilane. Such initiators are described in greater detail in U.S. Pat. Nos. 4,417,034 and 4,414,372, as is their use in the presence of selected anion and Lewis acid catalysts for the polymerization of acrylic and methacrylic monomers.

Farnham et al., in J. Am. Chem. Soc. 103, 4608 (1981) discuss structural aspects of the anionic pentacoordinate silicon compounds of the formulae

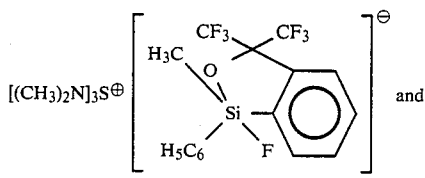 and

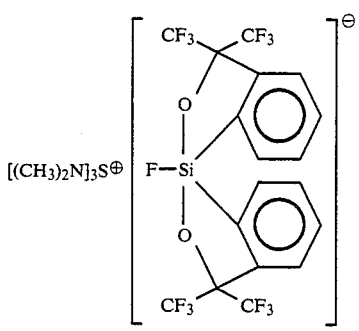

Perrozzi et al. in J. Am. Chem. Soc. 101, 1591 (1979) disclose similar pentacoordinate silicon compounds of the formula

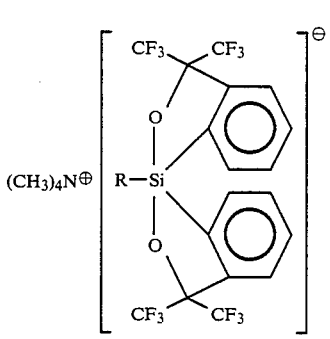

wherein R is methyl or phenyl.

It is an object of this invention to provide pentacoordinate silyl enolates which initiate polymerization of methacrylic monomers, including methacrylate esters, in the absence of catalysts, unlike the tetracoordinate silicon initiators of the art which require catalysts.

DETAILED DESCRIPTION OF THE INVENTION

This invention provides a process for polymerizing the monomer of the formula $$CH_2=C(CH_3)X \qquad (1)$$

wherein:
X is —C(O)X' or;
X' is —OSi(R$^1$)$_3$, —OR or —NR'R'';
each R$^1$, independently, is H or a hydrocarbyl radical which is an aliphatic, alicyclic, aromatic or mixed aliphatic-aromatic radical containing up to 20 carbon atoms; provided, however, at least one R$^1$ is not H;
R is a hydrocarbyl radical which is an aliphatic, alicyclic, aromatic or mixed aliphatic-aromatic radical containing up to 20 carbon atoms, optionally containing one or more ether oxygen atoms within aliphatic segments thereof, and optionally containing one or more functional substituents that are unreactive under polymerizing conditions; and each of R' and R" is independently selected from $C_{1-4}$ alkyl, the process comprising contacting the monomer under polymerizing conditions with the pentacoordinate silyl enolate initiator of the formula

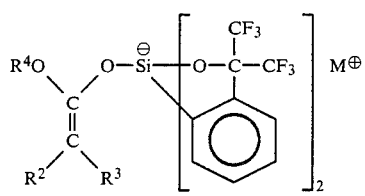

(2)

wherein:

each of $R^2$ and $R^3$ is independently selected from H or $C_{1-5}$ alkyl; provided, however, both $R^2$ and $R^3$ are not H;

$R^4$ is a hydrocarbyl radical which is an aliphatic, alicyclic, aromatic or mixed aliphatic-aromatic radical containing up to 20 carbon atoms, optionally containing one or more ether oxygen atoms within aliphatic segments thereof; and M is lithium, sodium, potassium or cesium, preferably lithium, to produce polymer comprising repeat units of the monomer.

By "polymerizing conditions" is meant in an inert anhydrous liquid medium at a temperature in the range of 20° C. to about 120° C. The polymerization pressure is not critical, although atmospheric pressure is preferred for economic advantage.

This invention also provides the enolate initiator 2, and a process for its preparation, wherein the process an alkali metal enolate is contacted and reacted with a known spiro silane, 3,3,3',3'-tetrakis(trifluoromethyl)-1,1'(3H,3'H)-spirobi(2,1-benzoxasilole), of the formula

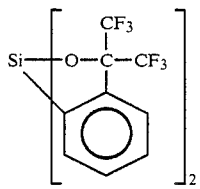

(3)

More specifically, in the invention process for preparing the enolate initiator 2, an alkali metal enolate of the formula $(R^2)(R^3)C=C(OR^4)O^{\ominus}M^{\oplus}$, wherein $R^2$, $R^3$, $R^4$ and M are as defined as above, is contacted and reacted in an anhydrous, inert solvent, such as tetrahydrofuran (THF) with the spiro silane 3 at a temperature in the range of about $-80°$ to about 25° C.

The alkali metal enolate is prepared by known methods which include, for example: (i) reaction of a ketene silyl acetal of the formula $(R^2)(R^3)C=C(OR^4)(OSi[R^1]_3)$, wherein $R^1$, $R^2$, $R^3$ and $R^4$ are as defined above, with an alkali metal alkyl, such as n-butyllithium; and (ii) reaction of an ester of the formula $(R^2)(R^3)CH-C(O)OR^4$, wherein $R^2$, $R^3$ and $R^4$ are as defined above, with lithium, sodium, potassium or cesium diisopropylamide. Preparative method (i) is preferred.

In preparing the enolate initiator 2, the silane 3 is added in an amount approximately equimolar to the alkali metal enolate. The enolate initiator 2 is recovered from the reaction mixture under an inert atmosphere by conventional procedures, for example, by solvent evaporation. Each reactant is normally present at a concentration of at least 1 weight %, preferably at least 10 weight %.

In the polymerization process of the invention, a solution of the enolate initiator 2 in an inert aprotic solvent, such as THF, toluene or "glyme" (dimethoxyethane), is contacted and reacted with the monomer 1 under polymerizing conditions. The amount of solvent used is at least sufficient to dissolve the normally solid initiator. Monomer 1, which is normally liquid, can be added directly to the initiator solution or it can be dissolved in a similar solvent and then added to the initiator solution. The relative molar amounts of monomer and initiator employed are such that the monomer/initiator molar ratio is at least 1, preferably at least 10.

Preferred enolates are those of formula 2 wherein $R^2$ and $R^3$ are $CH_3$ and $R^4$ is alkyl, most preferably methyl.

Preferred monomers are those of formula 1 wherein X is $-C(O)X'$ and X' is $-OR$; preferably, R is $C_{1-4}$ alkyl, most preferably methyl.

As indicated above, R in monomer 1 may contain functional substituents which are unreactive under polymerizing conditions. Such substituents include, but are not limited to, $-OSi(R^1)_3$, $-CO_2R$, $-OC(O)R$, $-NR'R''$, $-C(O)NR'R''$, $-CN$, $-OCH(R)OR$,

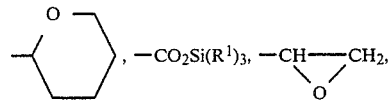

and $-SR$, wherein all symbols are defined as above. Such substituents, either directly or after a chemical treatment, for example, hydrolysis, provide functional sites along or at the ends of polymer chains, suitable for cross-linking, chain extension, chain branching or modification of properties, such as water and UV absorption.

Although not wishing to be bound by any particular mechanism, it is believed that in initiating the polymerizing of monomer 1 in the invention process, enolate 2 adds to the monomer with the formation of a new carbon-carbon bond and transfer of the spirosilicate moiety to monomer oxygen at the growing end of the polymer chain. The terminal spirosilicate moiety is readily removed by methanolysis. For example, in the polymerization of n moles of methyl methacrylate (MMA) wherein $n \geq 1$ and all other symbols are as defined above unless otherwise specified:

(4)

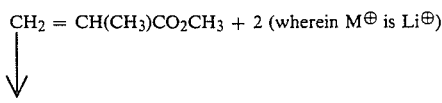

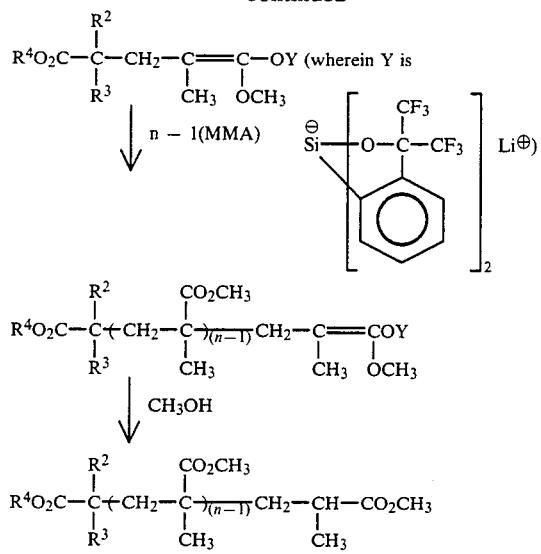

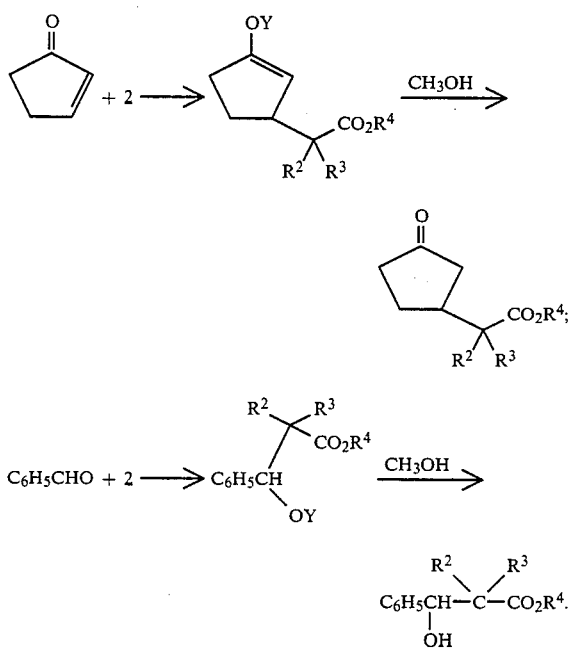

The enolate of formula 2 is also capable of adding to selected, non-polymerizing carbonyl compounds, the addition products, after methanolysis, containing useful new functionality. For example, the enolate can add to α,β-unsaturated ketones and aldehydes, illustrations of which include:

In the following examples of specific embodiments $\overline{M}_n$ and $\overline{M}_w$ represent number average and weight average molecular weights, respectively, and the polydispersity (D) of the polymer is defined by $D = \overline{M}_w/\overline{M}_n$. Molecular weights were determined by gel permeation chromatography (GPC). All temperatures are in degrees Celsius.

EXAMPLE 1

A. Preparation of the Pentacoordinate Silyl Enolate of Formula 2 Wherein $R^2$, $R^3$ and $R^4$ are $CH_3$ and M is Li A solution of [(1-methoxy-2-methyl-1-propenyl)oxy]-trimethylsilane (3.92 g, 22.5 mmol) in THF (40 mL) at ca. $-10°$ was treated with butyllithium (18.2 mmol), and the resulting solution was stirred at 0° for 4 minutes. The spiro silane 3 (9.23 g, 18.0 mmol) was added in one portion and the mixture was stirred for 1 h. Solvent was removed under vacuum and the flask was transferred to a dry box. Petroleum ether was added, and the precipitated solid was filtered, washed with petroleum ether and dried to give 11.2 g of the desired silyl enolate as a white crystalline solid, mp 108°–110°. $^{19}F$ NMR: (THF-d$_8$) (94.1 mHz) $-74.48$ (center of $A_3B_3$, approx. $\nu_A$, $\nu_B = -74.69$, $-74.27$, $J = 9$ Hz); at 376 mHz $\Delta\nu_{AB} = 195.4$ Hz. $^1H$ NMR: (360 mHz) 8.25–8.17 (m, 2H), 7.48–7.40 (m, 2H), 7.39–7.17 (m, 4H), 315 (s, 3H), 1.35 (s, 3H), 1.16 (s, 3H), and signals from two solvate THF molecules. Anal. Calcd. for $C_{31}H_{33}F_{12}O_6SiLi$: C, 48.69; H, 4.35. Found: C 48.35; H, 4.68.

B. Polymerization of Methyl Methacrylate (MMA)

A solution of the silyl enolate prepared in Part A (400 mg, 0.65 mmol) in anhydrous THF (15 mL) was treated with methyl methacrylate (5 mL) and heated at 60° for 2.0 h. Evaporation of solvent gave 3.35 g of white solid polymer (poly MMA). GPC analysis showed $\overline{M}_n = 8640$, $\overline{M}_w = 13,700$, D = 1.59; anticipated molecular weight based upon complete reaction of monomer was 7850. $^1H$ NMR (CDCl$_3$): 8.05–7.85 (m), 7.60–7.25 (m), 3.55 (s), 1.0 and 0.8 (CH$_3$ signals of nearly equal intensity). Reaction time was increased to 5.0 h without significant effect on the conversion of MMA to polymer. A control reaction carried out without the silyl enolate gave less than 10 mg of residue after evaporation of the volatiles.

EXAMPLE 2

A. Preparation of the Pentacoordinate Silyl Enolate of Formula 2 Wherein $R^4$ is Menthyl, $R^2$ and $R^3$ are $CH_3$ and M is Li A solution of [(1-menthoxy-2-methyl-1-propenyl)oxy]trimethylsilane (6.71 g, 22.5 mmol) in THF (40 mL) was treated with butyllithium (20.3 mmol) at 0°. After 4 minutes the spiro silane 3 (10.4 g, 20.3 mmol) was added in one portion and the mixture was stirred for 1 h. Solvent was removed under vacuum and the residue was treated with petroleum ether and cooled in a dry box. The resulting solid was filtered to give 13.1 g of the desired silyl enolate as a white solid. $^1H$ NMR: 8.45–8.10 (m), 7.60–7.10 (m), 1.70–0.50 (series of CH$_3$ and CH$_2$ signals), 0.10 (d, J=7 Hz). At 360 mHz, there were four methyl group signals at 1.37, 1.34, 1.23, and 1.15, and the ratio of diastereomers was ca 60/40.

B. Polymerization of Methyl Methacrylate

A solution of the silyl enolate prepared in Part A (0.5 g, 0.65 mmol) in dry THF (15 mL) was treated with methyl methacrylate (3.0 mL) and heated to reflux for 5.5 h. Evaporation of solvent gave 2.0 g of white solid polymer (poly MMA). GPC analysis showed $\overline{M}_n = 3110$, $\overline{M}_w = 5620$, D = 1.81; anticipated molecular weight based upon complete reaction of monomer was 5040.

A control reaction carried out without the silyl enolate gave less than 10 mg of residue after evaporation of the volatiles.

BEST MODE FOR CARRYING OUT THE INVENTION

The best mode presently contemplated for carrying out the invention is demonstrated by the examples.

INDUSTRIAL APPLICABILITY

The pentacoordinate silyl enolates of the invention are particularly useful as polymerization initiators for methacrylic monomers, especially the methacrylate esters.

I claim:

1. Process for polymerizing the monomer of the formula $CH_2=C(CH_3)X$ wherein

X is $-C(O)X'$ or;

X' is $-OSi(R^1)_3$, $-OR$ or $-NR'R''$;

each $R^1$, independently, is H or a hydrocarbyl radical which is an aliphatic, alicyclic, aromatic or mixed aliphatic-aromatic radical containing up to 20 carbon atoms; provided, however, at least one $R^1$ is not H;

R is a hydrocarbyl radical which is an aliphatic, alicyclic, aromatic or mixed aliphatic-aromatic radical containing up to 20 carbon atoms, optionally containing one or more ether oxygen atoms within aliphatic segments thereof, and optionally containing one or more functional substituents that are unreactive under polymerizing conditions; and each of R' and R'' is independently selected from $C_{1-4}$ alkyl, the process comprising contacting monomer, in an inert, anhydrous liquid medium, at a temperature in the range about 20° C. to about 120° C., with the pentacoordinate silyl enolate initiator of the formula

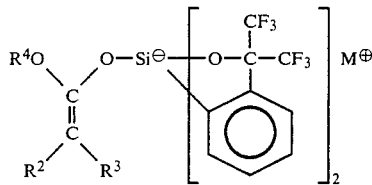

wherein each of $R^2$ and $R^3$ is independently selected from H or $C_{1-5}$ alkyl; provided, however, both $R^2$ and $R^3$ are not H;

$R^4$ is a hydrocarbyl radical which is an aliphatic, alicyclic, aromatic or mixed aliphatic-aromatic radical containing up to 20 carbon atoms, optionally containing one or more ether oxygen atoms within aliphatic segments thereof; and M is lithium, sodium, potassium or cesium.

2. Process of claim 1 wherein X is $-C(O)X'$ and X' is $-OR$.

3. Process of claim 2 wherein R is $C_{1-4}$ alkyl.

4. Process of claim 3 wherein R is methyl.

5. Process of claim 4 wherein $R^2$, $R^3$ and $R^4$ are methyl and M is lithium.

6. Process of claim 4 wherein $R^2$ and $R^3$ are methyl, $R^4$ is menthyl and M is lithium.

* * * * *